United States Patent [19]

Drengler

[11] Patent Number: 5,041,610

[45] Date of Patent: Aug. 20, 1991

[54] RESORCYCLIC ACID LACTONE DERIVATIVES AS ANIMAL GROWTH PROMOTANTS

[75] Inventor: Keith A. Drengler, Lindenhurst, Ill.

[73] Assignee: International Minerals & Chemical Corp., Northbrook, Ill.

[21] Appl. No.: 935,800

[22] Filed: Nov. 28, 1986

[51] Int. Cl.⁵ .......................... C07C 69/76; A23K 1/00
[52] U.S. Cl. ........................................ 560/64; 560/19; 560/23; 560/45; 560/47; 560/53; 560/66; 562/438; 562/452; 562/456; 562/459; 562/463; 562/474; 562/480; 426/635
[58] Field of Search ..................... 560/19, 23, 45, 47, 560/53, 64, 66; 562/438, 452, 456, 459, 463, 474, 480; 426/635

[56] References Cited

U.S. PATENT DOCUMENTS 3,901,921 8/1975 Urry ...................................... 560/64

FOREIGN PATENT DOCUMENTS 0116428 8/1984 European Pat. Off. .............. 560/64

Primary Examiner—Paul J. Killos
Attorney, Agent, or Firm—Wendell Ray Guffey; Thomas L. Farquer

[57] ABSTRACT

Ring-opened resorcyclic acid lactone derivatives of the formla

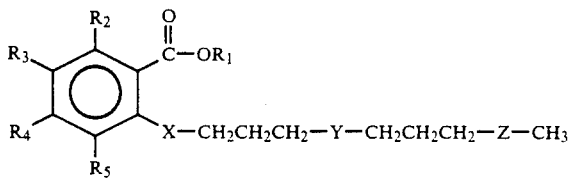

wherein X is ethylene or ethenylene; Y and Z, which may be the same or different, are methylene, hydroxymethylene or carbonyl; $R_1$ is hydrogen or lower alkyl of from 1 to about 6 carbon atoms; $R_2$, $R_3$, $R_4$ and $R_5$, which may be the same or different, are hydrogen, hydroxyl, halogen, nitro, amino or a radical selected from the group consisting of —R′, —OR′, —COOR′ and —OCOR′ wherein R′ is lower alkyl of from 1 to about 6 carbon atoms, lower cycloalkyl of from 3 to about 8 carbon atom, alkenyl of from 2 to about 6 carbon atoms, substituted or unsubstituted aryl of from 6 to about 8 carbon atoms, or substituted or unsubstituted aralkyl wherein the alkyl portion contains from 1 to about 6 carbon atoms and the aryl portion contains from 6 to about 8 carbon atoms. These compounds are useful as growth-promotants in food-producing animals.

40 Claims, No Drawings

RESORCYCLIC ACID LACTONE DERIVATIVES AS ANIMAL GROWTH PROMOTANTS

BACKGROUND OF THE INVENTION

1. Field of the Invention

The present invention relates to anabolic compounds and their use in promoting growth in food-producing animals

2. Description of the Background Art

A number of macrolide compositions of the general group known as resorcylic acid lactones (RAL's) and their derivatives are known to exhibit some level of anabolic activity, and are useful for promoting growth in food-producing animals Some resorcylic acid lactone derivatives are described by P. H. Hidy et al. in a publication entitled "Zearalenone and Some Derivatives: Production and Biological Activities", *Adv. Appl. Microbiol.*, 22:59-82, 1977. Zearalenone is a resorcylic acid lactone which exhibits anabolic properties when administered to certain animal species Some of its related derivatives, particularly zearalenone and zearalanol, possess significant anabolic properties.

Zearalenone is described in U.S. Pat. No. 3,196,019. Reduction of the olefinic group of zearalenone following the reduction procedure set forth in U.S. Pat. No. 3,239,341, by hydrogenation in the presence of palladium catalyst, will produce zearalenone, and complete reduction as disclosed in U.S. Pat. No. 3,239,345 will produce zearalanol Other related compounds which are known in the art include zearalene, zearalanol and zearalane.

Benzoic acid derivatives having side chains which may be closed to form a lactone ring are known in the art, but only as intermediates in the synthesis of RAL derivatives. See, e.g., U.S. Pat. No. 3,860,616 and 3,997,568.

There is an increasing need for anabolic substances for promoting growth in food-producing animals. It is important that the compositions to be used have the highest possible level of growth-promoting activity with minimal harmful side effects.

SUMMARY OF THE INVENTION

In accordance with the present invention, a method for promoting growth in a food-producing animal comprises administering to the animal a growth-promoting amount of a compound of the formula

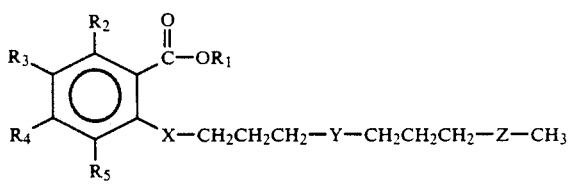

wherein X is ethylene or ethenylene; Y and Z, which may be the same or different, are methylene, hydroxymethylene or carbonyl; $R_1$ is hydrogen or lower alkyl of from 1 to about 6 carbon atoms; $R_2$, $R_3$, $R_4$ and $R_5$, which may be the same or different, are hydrogen, hydroxyl, halogen, nitro, amino or a radical selected from the group consisting of —R', —OR', —COOR' and —OCOR' wherein R' is lower alkyl of from 1 to about 6 carbon atoms, lower cycloalkyl of from 3 to about 8 carbon atoms, alkenyl of from 2 to about 6 carbon atoms, substituted or unsubstituted aryl of from 6 to about 8 carbon atoms, or substituted or unsubstituted aralkyl wherein the alkyl portion contains from 1 to about 6 carbon atoms and the aryl portion contains from 6 to about 8 carbon atoms. The present invention also relates to feed compositions comprising a nutrient and a growth-promoting amount of a compound so defined. The invention further relates to novel ring-opened resorcylic acid lactone derivatives encompassed by the above-defined structure.

DESCRIPTION OF THE PREFERRED EMBODIMENTS

According to one aspect, the present invention relates to a method for promoting growth in a food-producing animal comprising administering to the animal a growth-promoting amount of a compound of the formula

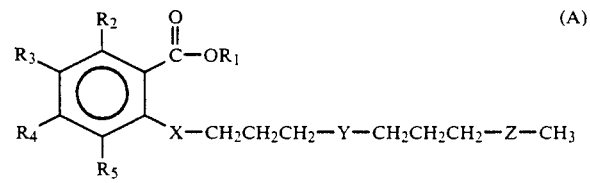

wherein X is ethylene or ethenylene; Y and Z, which can be the same or different, are methylene, hydroxymethylene or carbonyl; $R_1$ is hydrogen or lower alkyl of from 1 to about 6 carbon atoms such as methyl, ethyl, propyl, butyl, pentyl, hexyl and the like; $R_2$, $R_3$, $R_4$ and $R_5$, which may be the same or different, are hydrogen, hydroxyl, halogen, nitro, amino or a radical selected from the group consisting of —R', —OR', —COOR' and —OCOR' wherein R' is lower alkyl of from 1 to about 6 carbon atoms such as methyl, ethyl, propyl, butyl, pentyl, hexyl and the like, lower cycloalkyl of from 3 to about 8 carbon atoms such as cyclopropyl, cyclobutyl, cyclohexyl, cycloheptyl, cyclooctyl and the like, alkenyl of from 2 to about 6 carbon atoms such as ethenyl, propenyl, butenyl, pentenyl, hexenyl and the like, substituted or unsubstituted aryl of from 6 to about 8 carbon atoms such as phenyl, tolyl and the like, or substituted or unsubstituted aralkyl wherein the alkyl portion contains from 1 to about 6 carbon atoms and the aryl portion contains from 6 to about 8 carbon atoms, such as benzyl, tolylmethyl and the like.

These compounds are useful for promoting growth in food-producing animals, such as cattle, swine, sheep and poultry. They are particularly useful for promoting growth in ruminants such as cattle and sheep.

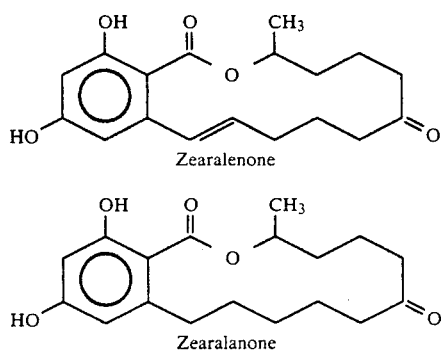

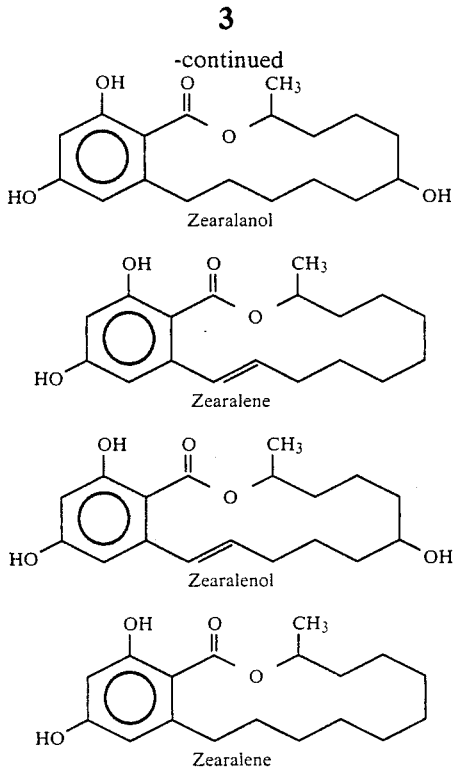

Zearalanol

Zearalene

Zearalenol

Zearalene

Methods for producing these starting compounds and their derivatives, including starting compound derivatives having aromatic ring substitutions, are described in the art as, for example, described in U.S. Pat. Nos. 2,196,019; 3,196,019; 3,239,341; 3,239,342; 3,239,345; 3,239,347; 3,239,348; 3,239,354; 3,239,356; 3,373,033; 3,373,037; 3,373,039; 3,551,454; 3,551,455; 3,624,144; 3,661,712; 3,687,982; 3,697,548; 3.860,616; 3,887,583; 3,954,805; 3,960,835; 3,960,898; 3,965,275; 3,989,828; 3,997,568; 4,004,978; 4,010,167; 4,035,504; 4,042,602; 4,052,414; 4,088,658; 4,148,808; 4,239,772; and 4,409,392; all of which are herein incorporated by reference.

The compounds and their derivatives may be produced under lactone-hydrolyzing reaction conditions according to the following general scheme, wherein X, Y, $R_2$, $R_3$, $R_4$, and $R_5$ are as defined above:

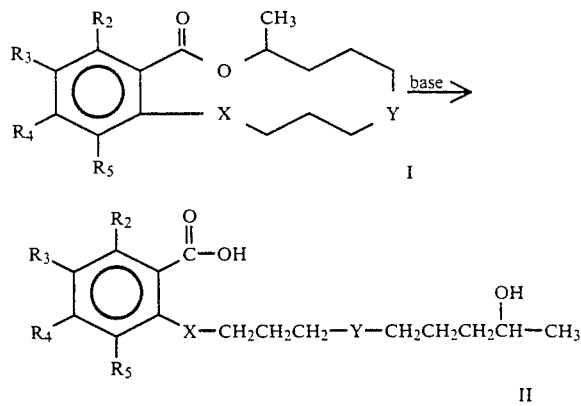

Compounds of the formula II can be further modified by, for example, aromatic or side chain substitutions, using procedures well known in the art. Substituted compounds derived from compounds of the formula II above, which substituted compounds also fall within the structural definition of formula A, are within the scope of this invention.

If desired, the carboxyl group shown in formula II above may be esterified as, for example, described in U.S. Pat. No. 3,997,568 to produce a compound of the formula III below, wherein $R_1$ is a lower alkyl, preferably from 1 to about 6 carbon atoms, most preferably methyl:

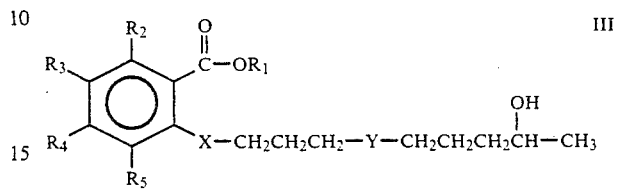

III

However, in preferred compounds, $R_1$ is hydrogen as shown in formula II, and $R_2$, $R_3$, $R_4$ and $R_5$, which may be the same or different, are hydrogen, hydroxyl, halogen, nitro, amino, the radical —R', wherein —R' is alkyl of 5 from 1 to about 3 carbon atoms or alkenyl of about 3 carbon atoms or the radical —OR', wherein R' is lower alkyl of from 1 to about 3 carbon atoms, alkenyl of about 3 carbon atoms, phenyl or benzyl.

In more preferred compounds for use in the method of the present invention, $R_1$, $R_2$, $R_3$, $R_4$ and $R_5$ are each hydrogen, or $R_1$ is hydrogen and at least one of $R_2$, $R_3$, $R_4$ and $R_5$ is hydroxyl, a methoxy radical or a benzyloxy radical, with the remainder of $R_2$, $R_3$, $R_4$ and $R_5$ being hydrogen. It is particularly preferred that $R_1$, $R_3$ and $R_5$ are hydrogen and one or both of $R_2$ and $R_4$, which may be the same or different, are hydroxyl, a methoxy radical or a benzyloxy radical.

Most preferably, $R_1$, $R_3$ and $R_5$ are hydrogen, and $R_2$ and $R_4$ are the same and are selected from the group consisting of hydrogen, hydroxyl and a benzyloxy radicals. Preferably, Z is hydroxymethylene. The RAL derivatives of this invention are not limited to any particular isomeric configuration.

The novel compounds of the invention are represented by the formula

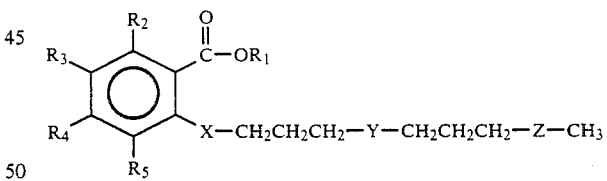

wherein X is ethylene or ethenylene; Y and Z, which may be the same or different, are methylene, hydroxymethylene or carbonyl; $R_1$ is hydrogen or lower alkyl of from 1 to about 6 carbon atoms; $R_2$, $R_3$, $R_4$ and $R_5$, which may be the same or different, are hydrogen, hydroxyl, halogen, nitro, amino or a radical selected from the group consisting of —R', —OR', —COOR' and —OCOR' wherein R' is lower alkyl of from 1 to about 6 carbon atoms, lower cycloalkyl of from 3 to about 8 carbon atoms, alkenyl of from 2 to about 6 carbon atoms, substituted or unsubstituted aryl of from 6 to about 8 carbon atoms, or substituted or unsubstituted aralkyl wherein the alkyl portion contains from 1 to about 6 carbon atoms and the aryl portion contains from 6 to about 8 carbon atoms, with the provisos that when $R_1$, $R_2$, $R_3$, $R_4$ and $R_5$ are hydrogen and X is ethylene, Y is hydroxymethylene or carbonyl; when $R_1$, R₂, R₃, R₄ and R₅ are hydrogen and Y is methylene, X is ethylene; when R₂ and R₄ are hydroxyl, R₁, R₃ and R₅ are hydrogen and X is ethylene, Y is carbonyl or hydroxymethylene; when R₂ and R₄ are hydroxyl, R₁, R₃ and R₅ are hydrogen and Y is methylene, X is ethenylene; when R₂ and R₄ are methoxy radicals, R₁, R₃ and R₅ are hydrogen and X is ethylene, Y is methylene; when R₂ and R₄ are methoxy radicals, R₁, R₃ and R₅ are hydrogen and X is ethenylene, Y is methylene or hydroxymethylene; and when R₂ and R₄ are benzyloxy radicals, R₁, R₃ and R₅ are hydrogen and X is ethylene or ethenylene, Y is methylene or hydroxymethylene. Preferably, Z is hydroxymethylene.

The compounds can be administered to animals by any suitable method including oral and parenteral administrations. For example, the compounds can be blended with ordinary feed compositions in amounts sufficient to produce the desired rate of growth and can thus be fed directly to the animals, or the compounds can be suspended in a suitable injection suspension medium, such as peanut oil, and injected parenterally. Alternatively, the compounds can be administered to animals by means of a subcutaneous implant as is well known in the art. The amount of compound administered to an animal, of course, varies depending upon the animal, desired rate of growth and the like.

When ring-opened RAL derivatives are to be administered in feeds, an animal feed composition may be prepared containing the usual nutritionally-balanced quantities of carbohydrates, proteins, vitamins and minerals, together with a ring-opened RAL derivative in accordance with the present invention. Some of the usual dietary elements included in animal feed compositions are grains, such as ground grain and grain by-products, animal protein substances, such as those found in fish meal and meat scraps, vegetable proteins, like soybean oil meal or peanut oil meal; vitamins and vitamin-containing materials, e.g., vitamin A and D mixtures, riboflavin supplements and other vitamin B complex members; and bone meal and limestone to provide minerals. A type of conventional feed material for use with cattle includes alfalfa hay and ground corncobs together with supplementary vitamins and vitamin-containing substances if desired.

It is preferable that the ring-opened RAL derivatives disclosed herein be administered to ruminants in amounts sufficient to be present in the animals rumenal fluid at concentrations of from about 5 ppm to about 1000 ppm, more preferably from about 20 ppm to about 500 ppm.

The invention is further illustrated by the following examples, which are not intended to be limiting.

EXAMPLE I 2-([10S]-10-hydroxyundecyl)-benzoic acid (A)

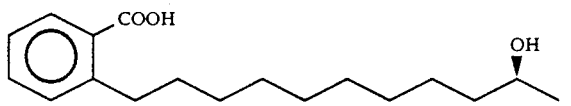

A solution of 18.04 g of dideoxyzearalane in 40 mL of 40% sodium hydroxide in water and 200 mL of dimethylsulfoxide was heated at reflux for 5.0 hours. The reaction was cooled, diluted with ice water, and acidified with 10% sulfuric acid. Insoluble material was removed by filtration and the filtrate was extracted with chloroform. The chloroform solution was dried over anhydrous magnesium sulfate, filtered, and concentrated under reduced pressure 9.61 g of crude product. Further purification was accomplished by column chromatography over silica gel. Purified compound A was an oil and exhibited the following spectral characteristics: IR 2927, 2855, 1706, 1254, 1016, 747 cm⁻¹; ¹H-NMR (CDCl₃) 1.22 (d), 1.33 (br), 3.05 (br), 3.90 (br), 6.88 (s), 7.33 (m), 8.07 (m); ¹³C-NMR (COCl₃) δ 23.33, 25.67, 29.36, 29.50, 31.74, 34.48, 39.27, 40.52, 68.30, 125.75, 129.05, 131.06, 131.31, 132.15, 145.34, 172.00.

EXAMPLE II 7,(2,4-dibenzyloxy-6-([6R,10S]-6,10-dihydroxyundecyl)benzoic acid (B)

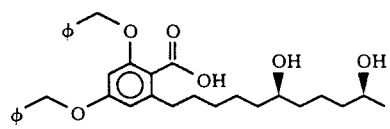

A. (6R)-2,4-Di-0-Benzylzeranol

A mixture of 50.02 g of zeranol (P-1496), 55.01 g of benzyl chloride, and 80.0 g of anhydrous potassium carbonate in 250 ml of dimethyl sulfoxide was stirred at 100° C. for 7 hours. The reaction was cooled to room temperature, diluted with 100 ml of water, and extracted 3 times with chloroform. The combined organic layer was washed with brine, dried over anhydrous magnesium sulfate, and concentrated under reduced pressure to provide 91.0 g of an oil. Column chromatography over silica gel using a gradient of methanol in methylene chloride provided 68.2 g (87%) of dibenzyl P-1496 as an oil. Crystallization from ether/hexane gave pure product with the following characteristics: mp 98°-9° C.; ¹H—NMR (CDCl₃) δ 1.17 (d), 5.03, 5.07 (2s), 6.52 (s), 7.40, 7.43 (2s).

B. Hydrolysis

A solution of 21.84 g 2,4-0-dibenzyl P-1496 in 60 ml of aqueous 40% sodium hydroxide and 200 ml of dimethyl sulfoxide was heated at reflux for 24 hours. The cooled solution was poured into 200 ml of water and extracted with methylene chloride. The combined organic phase was washed with water, dried over anhydrous magnesium sulfate, and concentrated under reduced pressure to furnish 12.40 g. Recrystallization from benzene provided 11.35 g of compound B as a white solid: mp 85°-7° C.; IR (KBr) 2933, 2859, 1703, 1602, 1166, 745 cm⁻¹; ¹H-NMR (CDCl₃) δ 1.21 (d), 1.41 (br), 5.01 (s), 5.07 (s), 5.55 (br), 6.48 (s), 7.37 (s); ¹³C-NMR (CDCl₃) 21.59, 23.26, 24.82, 29.07, 30.89, 33.98, 36.78, 37.00, 38.96, 68.09, 70.16, 71.00, 71.80, 108.41, 116.12, 127.11, 127.47, 127.91, 128.06, 128.28, 128.55, 136.38, 136.54, 144.75, 157.48, 160.64, 169.81.

EXAMPLE III 2,4-dihydroxy-6-([6R,10S]-6,10-dihydroxyundecyl)benzoic acid

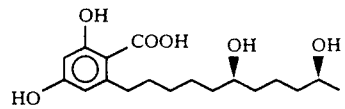

A mixture of 6.00 g of compound B from Example II and 6.03 g of 5% palladium on charcoal in 100 mL of ethanol was treated with hydrogen gas at a constant pressure of 50 psi for 5.0 hours at room temperature. The reaction was filtered through celite and concentrated under reduced pressure to provide 3.52 g of crude product. Recrystallization from aqueous ethanol furnished material with the following characteristics: mp 116°–8° C.; IR (KBr) 2993, 2860, 1660, 1540, 1225, 849 cm$^{-1}$; $^1$H-NMR (DMSO-d6) δ 1.07 (d), 1.35 (brm), 6.11 (s), 6.18 (s), 7.00 (br); $^{13}$C-NMR (DMSO) δ 21.65, 23.57, 25.09, 29.36, 31.39, 35.40, 43.64, 65.88, 69.64, 100.55, 104.84, 110.04, 147.31, 161.58, 172.65.

EXAMPLE IV 2-([6R,10S]-6,10-dihydroxyundecyl)-benzoic acid (C)

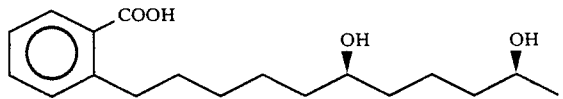

A. Preparation of Dideoxyzeranol

A mixture of 11.23 g of zeranol (P-1496), 15.75 g of 5-chloro-1-phenyl-1H-tetrazole, and 8.57 g of anhydrous potassium carbonate in 80 mL of methylethyl ketone was heated at reflux for 48 hours. The reaction was diluted with 100 mL of water and extracted with methylenechloride. The organic phases were combined, washed with water, dried over anhydrous magnesium sulfate, filtered, and concentrated under reduced pressure to give 23.31 g of crude product. Recrystallization from ethanol gave 18.00 g of the bisphenyltetrazole derivative of zeranol as a white solid: mp 106°–107° C.

A mixture of 30.03 g of the above product and 10.04 g of 5% palladium on charcoal in 1.0 L of ethanol was treated with hydrogen at a pressure of 500 psi at 70° C. for 6.0 hours. The cooled reaction mixture was filtered through celite and concentrated under reduced pressure to give 26.40 g of a crude solid. The solid was suspended in cyclohexane and heated at reflux for 5.0 hours. The insoluble phenyltetrazolone by-product was removed by filtration. The filtrate was washed with 3N hydrochloric acid, dried over anhydrous magnesium sulfate, and concentrated under reduced pressure to give 14.25 g of crude product. Recrystallization from a mixture of dichloromethane in hexane provided 12.87 g of dideoxyzeranol as a white solid: mp 63°–5° C.; IR (KBr) 3612, 2949, 2855, 1681, 1248, 1089, 759 cm$^{-1}$; $^1$H—NMR (CDCl$_3$) δ 1.05-185 (br), 3.92 (brm), 5.40 (br), 7.20–7.90 (m); $^{13}$—C—NMR (CDCl$_3$) δ 20.96, 21.03, 26.83, 30.96, 31.13, 33.52, 33.75, 35.28, 69.84, 70.75, 119.55, 125.46, 127.62, 129.34, 129.70, 130.54, 131.26, 131.68, 143.13, 168.41.

B. Hydrolysis

A solution of 8.10 g of dideoxyzeranol in 35 mL of 40% sodium hydroxide in water and 100 ml of dimethyl sulfoxide was heated at reflux for 24 hours. The solution was diluted with 150 ml of water, and extracted with dichloromethane to remove unreacted starting material. The basic aqueous layer was acidified with 10% sulfuric acid and extracted with dichloromethane. The organic phase was washed with water, dried over anhydrous magnesium sulfate, and concentrated under reduced pressure to give 8.16 g of an orange oil. Recrystallization from dichloromethane in hexane gave 7.85 g of compound C as a white solid: mp 64°–6° C.; IR (KBr) 3378, 2928, 2858, 1705, 1250, 1017, 749 cm$^{-1}$; $^1$H—NMR (CDCl$_1$) δ 1.22 (d), 1.47 (br), 3.03 (br), 3.75 (br), 5.33 (br), 7.37 (m), 8.00 (m); $^{13}$C—NMR (CDCl$_3$) δ 21.57, 23.30, 24.87, 29.26, 31.45, 34.23, 36.82, 37.04, 38.96, 71.78, 125.69, 129.00, 130.99, 131.21, 132.22, 145.20, 171.29.

EXAMPLE V 2-([6R,10S]-6,10-Dihydroxyundecyl)-4-benzyloxybenzoic acid

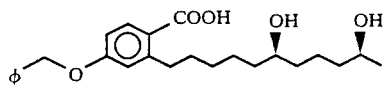

A. preparation of 2-deoxyzeranol

A mixture of 50.04 g of zeranol, 50.03 g of anhydrous potassium carbonate, and 22.80 g of benzyl chloride in 1.0 L of dry acetone was heated at reflux for 24 hours. The reaction mixture was filtered to remove the solids and concentrated under reduced pressure to provide 61.06 g of an oil. Crystallization from aqueous ethanol furnished 52.51 g of 4-0-benzylzeranol as a white solid: mp 121°–3° C.; $^1$H-NMR (CDCl$_3$) δ 1.37 (d), 1.60 (br), 5.07 (s), 6.50 (s), 7.40 (s).

A mixture of 19.62 g of 4-benzylzeranol, 13.00 g of potassium carbonate, and 12.60 g of 5-chloro-1-phenyl-1H-tetrazole in 95 mL of dry 2-butanone was heated at reflux for 68 hours. The reaction was cooled, diluted with 100 ml of dichloromethane, washed with water, dried over anhydrous magnesium sulfate, and concentrated under reduced pressure to provide 22.08 g of crude product Recrystallization from aqueous ethanol provided 21.76 g of 2-0-phenyltetrazoyl-4-0-benzylzeranol: mp 118°–9° C.; $^1$H—NMR (CDCl$_3$) δ 0.80 (d), 1.40 (br), 2.76 (br), 3.72 (br), 5.01 (s), 6.92 (d), 7.36 (s), 7.60–7.96 (m).

A mixture of 50.00 g of 2-0-phenyltetrazoyl-4-0-benzylzeranol and 15.40 g 5% palladium on charcoal in 1.2L of ethanol was treated with hydrogen at a pressure of 500 psi at 70° C. for 4.0 hours The cooled reaction mixture was filtered through celite and concentrated under reduced pressure to give 52.31 g of crude product. The solid was suspended in warm dichloromethane and the insoluble 2-deoxyzeranol was collected by filtration. Recrystallization from aqueous ethanol provided 23.21 g of pure material mp 177°–8° C.; IR (KBr) 3417, 3174, 2946, 1680, 1605, 1458, 1245, 1122 cm$^{-1}$; $^1$H—NMR (DMSO—Cl$_6$) δ 1.01–1.09 (br), 2.50–3.00 (br m), 3.05–3.78 (br m), 5.00–5.51 (br), 6.75 (m), 6.88 (s), 7.75 (m); $^{13}$C—NMR (DMSO—Cl$_6$) δ 20.69, 20.77, 26.29, 30.42, 30.79, 33.10, 33.36, 34.75, 38.15, 68.43, 68.49, 112.71, 116.81, 121.46, 131.86, 145.39, 160.21, 167.05.

B. Preparation of 4-0-benzyl-2-deoxyzeranol

A mixture of 5.02 g of 2-deoxyzeranol, 4.15 g of benzyl chloride, and 4.54 g of anhydrous potassium carbonate in 200 mL of 2-butanone was heated at reflux for 29 hours. The mixture was cooled and filtered. The filtrate was concentrated under reduced pressure to give 7.61 g of an oil. Recrystallization from a mixture of ethyl acetate and hexane provided 5.98 g of 4-0-benzyl-2-deoxyzeranol: mp 80°–1° C.; IR (KBr) 3386, 2942, 2853, 1690, 1599, 1460, 1246, 1006, 741, 702 cm$^{-1}$; $^1$H—NMR (CDCl$_3$) δ 1.25–2.00 (br m), 5.13 (s), 6.55 (m), 6.95 (s), 7.45 (s), 7.85 (m); $^{13}$C—NMR (CDCl$_3$) δ 21.09, 26.69, 31.16, 31.33, 33.52, 33.92, 35.32, 69.33, 69.98, 70.64, 111.77, 116.73, 123.94, 127.44, 128.06, 128.58, 132.27, 136.53, 146.12, 161.10, 167.76.

C. Hydrolysis

A solution consisting of 10.24 of 4-0-benzyl-2-deoxyzeranol in 60 mL of 40% sodium hydroxide and 120 mL of dimethyl sulfoxide was heated at reflux for 24 hours. The reaction was cooled, diluted with 100 mL of water and extracted with dichloromethane. The basic aqueous solution was acidified with 10% sulfuric acid and extracted with dichloromethane. The organic layers were combined, washed with water, dried over anhydrous magnesium sulfate, and concentrated under reduced pressure to provide 11.23 g of an oil. Recrystallization from 5% hexane in dichloromethane provided 9.63 g of the title compound as a white solid: mp 107°–9° C.; IR (KBr) 3940, 3269, 2925, 2857, 1679, 1604, 1585, 1248, 1154, 659 cm$^{-1}$; $^1$H—NMR (CDCl$_3$) 1.17 (d), 1.43 (br), 3.00 (br), 3.67 (br), 5.07 (s), 6.83 (br), 7.40 (s), 8.00 (d); $^{13}$C—NMR (CDCl$_3$) δ 21.65, 23.41, 24.97, 29.35, 31.34, 34.78, 36.96, 37.13, 39.05, 68.16, 70.04, 71.78, 111.75, 117.40, 121.01, 127.48, 128.14, 128.32, 128.64, 134.06, 136.42, 148.54, 161.99, 170.94.

EXAMPLE VI 4-hydroxy-2-(6R,10S-6,10-dihydroxyundecyl)benzoic acid

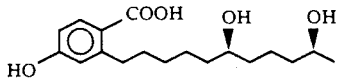

A solution of 2.01 g of 2-deoxyzeranol in 50 mL of 20% sodium hydroxide was heated at reflux for 6.5 hours. The solution was cooled to room temperature, acidified with concentrated hydrochloric acid, and extracted with dichloromethane. The combined organic layer was washed with water dried over anhydrous magnesium sulfate, and concentrated under pressure to give 2.68 g of an oil. Recrystallization from aqueous ethanol provided 1.87 g of the title compound: mp 84°–6° C.; IR (KBr) 2934, 2857, 1603, 1573, 1234, 789 cm$^{-1}$; $^1$H—NMR (DMSO—d$_6$) δ 1.10 (d), 1.40 (br), 3.00 (br), 3.50 (br), 4.32 (br), 6.83 m), 7.87 (d); $^{13}$C—NMR (DMSO—d$_6$) δ 21.56, 23.46, 25.03, 29.45, 31.46, 34.08, 37.87, 37.99, 39.03, 40.16, 66.22, 69.96, 112.87, 117.45, 120.61, 133.26, 147.10, 160.44, 168.42.

EXAMPLE VII 6-([6R,10S]-6,10-dihydroxyundecyl)-2-benzyloxybenzoic acid

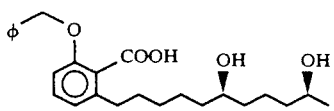

A. Preparation of 4-deoxyzeranol

A mixture of 50.06 g of zeranol, 21.52 g of anhydrous potassium carbonate, and 28.09 g of 5-chloro-1-phenyl-1H-tetrazole in 500 mL of dry acetone was heated at reflux for 48 hours. The cooled reaction was filtered and concentrated. The oil was dissolved in hot chloroform and allowed to stand overnight at room temperature. The insoluble starting material was removed by filtration. The filtrate was extracted with several portions of 10% sodium hydroxide solution. The basic aqueous layers were combined, acidified with concentrated hydrochloric acid and extracted with chloroform. The organic layers were combined, dried over anhydrous magnesium sulfate, filtered, concentrated, and recrystallized from ethanol to give 25.2 g of 4-0-phenyltetrazoylzeranol: mp 142°–4° C.

A mixture of 32.75 g of 4-0-phenyltetrazoylzeranol and 10.79 g of 5% palladium on charcoal in 1000 ml of ethanol was treated with hydrogen at a pressure of 500 psi and 70° C. for 4.5 hours. The cooled reaction mixture was filtered through celite and concentrated under reduced pressure to give 33.51 g of crude product. The crude product was stirred in hot dichloromethane until all the solids dissolved. The solution was allowed to cool to room temperature and the precipitated phenyltetralone byproduct was collected by filtration. The filtrate was diluted with hexane and cooled at 0° C. The solid was collected by filtration to give 15.58 g of 4-deoxyzeranol: mp 79°–80° C.; IR (KBr) 3370, 2919, 2859, 1647, 1452, 1101 cm$^{-1}$; $^1$H—NMR (CDCl$_3$) δ 1.21 (d), 3.15 (br), 3.76 (br), 5.23 (br), 5.30 (s), 6.80 (t), 7.23 (m), 11.50 (s); $^{13}$C—NMR (CDCl$_3$) δ 21.19, 21.46, 23.62, 27.21, 31.40, 32.11, 35.22, 35.91, 36.61, 68.81, 73.86, 112.07, 115.75, 122.34, 134.11, 146.14, 163.02, 171.63.

B. Preparation of 2-0-benzyl-4-deoxyzeranol

A mixture of 8.10 g of 4-deoxyzeranol, 16.52 g of anhydrous potassium carbonate, and 2.00 mL of dry 2-butanone was heated at reflux for 48 hours. The cooled solution was filtered and concentrated to give 9.34 g of a yellow oil. Column chromatography over silica gel using 10% acetone/hexane furnished 8.76 g of 2-0-benzyl-4-deoxyzeranol: mp 62°–3° C.; IR (KBr) 3429, 2994, 2884, 1717, 1268, 1109, 1084 cm$^{-1}$; $^1$H—NMR (CDCl$_3$) 1.15 (d), 1.42 (br), 2.57 (br), 3.81 (br), 5.0 (s), 6.84 (t), 7.34 (m), 7.38 (s); $^{13}$C—NMR (CDCl$_3$) δ 19.31, 20.41, 20.59, 27.14, 29.44, 31.62, 32.89, 33.75, 35.35, 70.65, 70.71, 70.95, 109.76, 121.69, 124.92, 127.55, 127.91, 128.37, 129.98, 136.73, 140.96, 155.56, 168.36.

C. Hydrolysis

A solution of 3.70 g of 2-0-benzyl-4-deoxyzeranol in 35 ml of 40% sodium hydroxide and 50 ml of dimethyl sulfoxide was heated at reflux for 24 hours. The cooled solution was washed with 200 ml of water and extracted with dichloromethane to remove any unreacted starting material. The aqueous layer was acidified with concentrated sulfuric acid and extracted with several portions of dichloromethane. The combined organic solution was washed with water, dried over anhydrous magnesium sulfate, filtered and concentrated to give 3.00 g of a yellow oil. Column chromatography over silica gel using 10% ethanol in hexane as eluant gave 2.01 g of the title product as a clear oil: IR (film) 3551, 2992, 2860, 1717, 1581, 1457, 1286, 1025 cm$^{-1}$; $^1$H—NMR (CDCl$_3$) δ 1.15 (d), 1.40 (br), 5.15 (s), 6.80 (m), 7.30 (m), 7.38 (s); $^{13}$C—NMR (CDCl$_3$) δ 21.59, 23.34, 24.80, 29.01, 30.83, 33.19, 36.81, 37.06, 39.02, 68.01, 70.72, 71.72, 110.23, 122.11, 124.80, 127.22, 127.76, 128.44, 129.91, 136.94, 141.52, 155.31, 170.10.

EXAMPLE VIII 2-hydroxy-6-([6R,10S]-6,10-dihydroxyundecyl)-benzoic acid

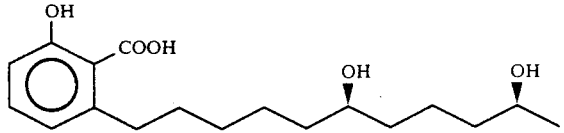

A mixture of 1.64 g of the final product in Example VI, 2.02 g of 5% palladium on charcoal, and 100 ml of ethanol was treated with hydrogen maintained at a pressure of 50 psi at room temperature for 5 hours. The reaction mixture was filtered through celite, concentrated and recrystallized from a mixture of acetone in hexane to give 0.68 g of the title compound: mp 83°-4° C.; IR (KBr) 3329, 2909, 2858, 1590, 1468, 1126, 1023 cm$^{-1}$; $^1$H—NMR (DMSO—d$_6$) δ 1.05 (d), 1.30 (br), 6.38 (t), 6.92 (t); $^{13}$C—NMR (DMSO—d$_6$) δ 21.56, 23.49, 25.20, 29.55, 31.83, 34.65, 36.35, 39.19, 65.75, 69.56, 113.88, 118.44, 118.74, 129.41, 145.60, 163.85, 172.07.

EXAMPLE IX

Using procedures generally described above, ring-opened RAL's having the structure shown in formula A above and which are effective in promoting growth when administered to animals are synthesized with the following substituents:

```
X  = ethylene, ethenylene
Y  = methylene, hydroxymethylene, carbonyl
Z  = methylene, hydroxymethylene, carbonyl
R₁ = —H, —CH₃, —C₂H₅, —C₃H₇, —C₄H₉, —C₅H₁₁, —C₆H₁₃
R₂ = —H, —OH, —F, —NO₂, —NH₂, —CH₃, —C₂H₅, —C₃H₇,
     —C₄H₉, —C₅H₁₁, —C₆H₁₃, —OCH₃, —OC₂H₅, —OC₃H₇,
     —OC₄H₉, —OC₅H₁₁, —OC₆H₁₃, —COOCH₃,
     —COOC₂H₅, —COOC₃H₇, —COOC₄H₉, —COOC₅H₁₁,
     —COOC₆H₁₃, —OCOCH₃, —OCOC₂H₅, —OCOC₃H₇,
     —OCOC₄H₉, —OCOC₅H₁₁, —OCOC₆H₁₃, cyclopropyl,
     cyclobutyl, cyclohexyl, cycloheptyl,
     cyclooctyl, ethenyl, propenyl, butenyl,
     pentenyl, hexenyl, phenyl, tolyl, benzyl,
     tolylmethyl
R₃ = —H, —OH, —F, —NO₂, —NH₂, —CH₃, —C₂H₅, —C₃H₇,
     —C₄H₉, —C₅H₁₁, —C₆H₁₃, —OCH₃, —OC₂H₅, —OC₃H₇,
     —OC₄H₉, —OC₅H₁₁, —OC₆H₁₃, —COOCH₃,
     —COOC₂H₅, —COOC₃H₇, —COOC₄H₉, —COOC₅H₁₁,
     —COOC₆H₁₃, —OCOCH₃, —OCOC₂H₅, —OCOC₃H₇,
     —OCOC₄H₉, —OCOC₅H₁₁, —OCOC₆H₁₃, cyclopropyl,
     cyclobutyl, cyclohexyl, cycloheptyl,
     cyclooctyl, ethenyl, propenyl, butenyl,
     pentenyl, hexenyl, phenyl, tolyl, benzyl,
     tolylmethyl
R₄ = —H, —OH, —F, —NO₂, —NH₂, —CH₃, —C₂H₅, —C₃H₇,
     —C₄H₉, —C₅H₁₁, —C₆H₁₃, —OCH₃, —OC₂H₅, —OC₃H₇,
     —OC₄H₉, —OC₅H₁₁, —OC₆H₁₃, —COOCH₃, —COOC₂H₅,
     —COOC₃H₇, —COOC₄H₉, —COOC₅H₁₁, —COOC₆H₁₃,
     —OCOCH₃, —OCOC₂H₅, —OCOC₃H₇, —OCOC₄H₉,
     —OCOC₅H₁₁, —OCOC₆H₁₃, cyclopropyl,
     cyclobutyl, cyclohexyl, cycloheptyl,
     cyclooctyl, ethenyl, propenyl, butenyl,
     pentenyl, hexenyl, phenyl, tolyl, benzyl,
     tolylmethyl
R₅ = —H, —OH, —F, —NO₂, —NH₂, —CH₃, —C₂H₅, —C₃H₇,
     —C₄H₉, —C₅H₁₁, —C₆H₁₃, —OCH₃, —OC₂H₅, —OC₃H₇,
     —OC₄H₉, —OC₅H₁₁, —OC₆H₁₃, —COOCH₃, —COOC₂H₅,
     —COOC₃H₇, —COOC₄H₉, —COOC₅H₁₁, —COOC₆H₁₃,
     —OCOCH₃, —OCOC₂H₅, —OCOC₃H₇, —OCOC₄H₉,
     —OCOC₅H₁₁, —OCOC₆H₁₃, cyclopropyl,
     cyclobutyl, cyclohexyl, cycloheptyl,
     cyclooctyl, ethenyl, propenyl, butenyl,
     pentenyl, hexenyl, phenyl, tolyl, benzyl,
     tolylmethyl
```

EXAMPLE X

Effects of Ring-opened RAL's on in vitro Ruminant Voltile Fatty Acids

The effect of ring-opened RALs on ruminant volatile fatty acid production was tested in vitro. A low acetate to propionate ratio indicates a shift from acetate towards propionate production which predicts increased feed utilization benefits to the ruminant.

Rumen fluid was removed from fistulated steers and strained through cheesecloth. An equal amount of pH 7 buffer was added to the strained rumen fluid. Buffered rumen fluid, finely ground fresh cattle ration and cellubiose were mixed at a ratio of about 10,000:500:1 by weight, respectively, and then reacted with between 5 and 500 ppm of test compound in fermenters using an incubator shaker for 24 hours at 38° C.

Experimental samples were tested against control samples not containing test compounds (negative control), as well as control samples containing bromoethane sulfonic acid (positive control), a material known to shift the volatile fatty acid production in rumen fluid towards propionate.

The experimental compounds tested are shown below, and test results are shown in Table I.

TABLE I

[Structures (i) and (ii) shown]

| Test Compound | Acetate (μmol/ml) | Proprionate (μmol/ml) | A/P |
|---|---|---|---|
| Negative control | 106.3 | 34.7 | 3.04 |
| i | 81.1 | 40.5 | 2.00 |
| ii | 87.2 | 57.7 | 1.51 |
| Positive control | 72.3 | 39.7 | 1.82 |

The results indicate that the tested ring-opened RALs are effective in shifting rumen fluid volatile fatty acids towards propionate.

I claim:

1. A method for promoting growth in a food-producing animal which comprises administering to said animal a growth-promoting amount of a compound of the formula

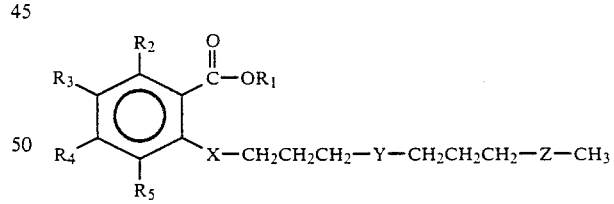

wherein X is ethylene or ethenylene; Y and Z, which may be the same or different, are methylene, hydroxymethylene or carbonyl; R$_1$ is hydrogen or lower alkyl of from 1 to about 6 carbon atoms; R$_2$, R$_3$, R$_4$ and R$_5$, which may be the same or different, are hydrogen, hydroxyl, halogen, nitro, amino or a radical selected from the group consisting of —R', —OR', —COOR' and —OCOR' wherein R' is lower alkyl of from 1 to about 6 carbon atoms, lower cycloalkyl of from 3 to about 8 carbon atoms, alkenyl of from 2 to about 6 carbon atoms, substituted or unsubstituted aryl of from 6 to about 8 carbon atoms, or substituted or unsubstituted aralkyl wherein the alkyl portion contains from 1 to about 6 carbon atoms and the aryl portion contains from 6 to about 8 carbon atoms.

2. The method of claim 1 wherein $R_1$ is hydrogen.

3. The method of claim 2 wherein $R_2$, $R_3$, $R_4$ and $R_5$, which may be the same or different, are hydrogen, hydroxyl, halogen, nitro, amino, alkyl of from 1 to about 3 carbon atoms, alkenyl of about 3 carbon atoms, or the radical —OR' wherein R' is lower alkyl of from 1 to about 3 carbon atoms, alkenyl of about 3 carbon atoms, phenyl or benzyl.

4. The method of claim 3 wherein $R_3$ and $R_5$ are hydrogen.

5. The method of claim 4 wherein $R_2$ and $R_4$, which may be the same or different, are hydrogen, hydroxyl methoxy radical or benzyloxy radical.

6. The method of claim 5 wherein $R_2$ and $R_4$ are benzyloxy radicals.

7. The method of claim 6 wherein X is ethenylene and Y is hydroxymethylene.

8. The method of claim 6 wherein X is ethylene and Y is hydroxymethylene.

9. The method of claim 5 wherein $R_2$ and $R_4$ are hydrogen.

10. The method of claim 9 wherein X is ethylene and Y is methylene.

11. The method of claim 9 wherein X is ethylene and Y is hydroxymethylene.

12. The method of claim 5 wherein $R_2$ and $R_4$ are hydroxyl.

13. The method of claim 12 wherein X is ethylene and Y is hydroxymethylene.

14. The method of claim 1 wherein Z is hydroxymethylene.

15. A feed composition comprising a nutrient and a growth-promoting amount of a compound of the formula

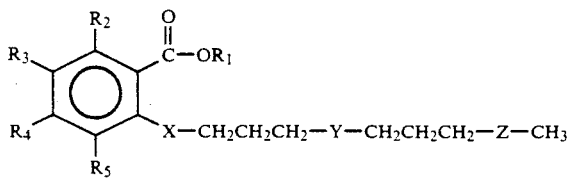

wherein X is ethylene or ethenylene; Y and Z, which may be the same or different, are methylene, hydroxymethylene or carbonyl; $R_1$ is hydrogen or lower alkyl of from 1 to about 6 carbon atoms; $R_2$, $R_3$, $R_4$ and $R_5$, which may be the same or different, are hydrogen, hydroxyl, halogen, nitro, amino or a radical selected from the group consisting of —R', —OR', —COOR' and —OCOR' wherein R' is lower alkyl of from 1 to about 6 carbon atoms, lower cycloalkyl of from 3 to about 8 carbon atoms, alkenyl of from 2 to about 6 carbon atoms, substituted or unsubstituted aryl of from 6 to about 8 carbon atoms, or substituted or unsubstituted aralkyl wherein the alkyl portion contains from 1 to about 6 carbon atoms and the aryl portion contains from 6 to about 8 carbon atoms.

16. The feed composition of claim 16 wherein $R_1$ is hydrogen.

17. The feed composition of claim 16 wherein $R_2$, $R_3$, $R_4$ and $R_5$, which may be the same or different, are hydrogen, hydroxyl, halogen, nitro, amino, alkyl of from 1 to about 3 carbon atoms, alkenyl of about 3 carbon atoms, or the radical —OR' wherein R' is lower alkyl of from 1 to about 3 carbon atoms, alkenyl of about 3 carbon atoms, phenyl or benzyl.

18. The feed composition of claim 17 wherein $R_3$ and $R_5$ are hydrogen.

19. The feed composition of claim 18 wherein $R_2$ and $R_4$, which may be the same or different, are hydrogen, hydroxyl, methoxy radical or benzyloxy radical.

20. The feed composition of claim 19 wherein $R_2$ and $R_4$ are benzyloxy radicals.

21. The feed composition of claim 20 wherein X is ethenylene and Y is carbonyl.

22. The feed composition of claim 20 wherein X is ethylene and Y is hydroxymethylene.

23. The feed composition of claim 18 wherein $R_2$ and $R_4$ are hydrogen.

24. The feed composition of claim 23 wherein X is ethylene and Y is methylene.

25. The feed composition of claim 23 wherein X is ethylene and Y is hydroxymethylene.

26. The feed composition of claim 19 wherein $R_2$ and $R_4$ are hydroxyl.

27. The feed composition of claim 26 wherein X is ethylene and Y is hydroxymethylene.

28. The feed composition of claim 15 wherein Z is hydroxymethylene.

29. A compound of the formula

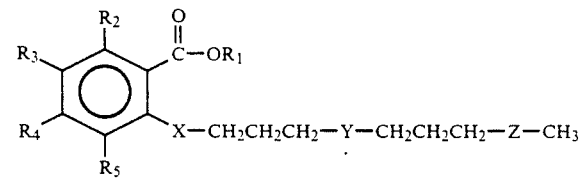

wherein X is ethenylene; Y and Z, which may be the same or different, are methylene, hydroxymethylene or carbonyl; $R_1$ is hydrogen or lower alkyl of from 1 to about 6 carbon atoms; $R_2$, $R_3$, $R_4$ and $R_5$, which may be the same or different, are hydrogen, hydroxyl, halogen, nitro, amino or a radical selected from the group consisting of —R', —OR', —COOR' and —OCOR' wherein R' is lower alkyl of from 1 to about 6 carbon atoms, lower cycloalkyl of from 3 to about 8 carbon atoms, alkenyl of from 2 to about 6 carbon atoms, substituted or unsubstituted aryl of from 6 to about 8 carbon atoms, or substituted or unsubstituted aralkyl wherein the alkyl portion contains from 1 to about 6 carbon atoms and the aryl portion contains from 6 to about 8 carbon atoms, with the provisos that when $R_1$, $R_2$, $R_3$, $R_4$ and $R_5$ are hydrogen and X is ethylene, Y is hydroxymethylene or carbonyl; when $R_1$, $R_2$, $R_3$, $R_4$ and $R_5$ are hydrogen and Y is methylene, X is ethylene; when $R_2$ and $R_4$ are hydroxyl, $R_1$, $R_3$ and $R_5$ are hydrogen and X is ethylene, Y is carbonyl or hydroxymethylene; when $R_2$ and $R_4$ are hydroxyl, $R_1$, $R_3$ and $R_5$ are hydrogen and Y is methylene, X is ethenylene; when $R_2$ and $R_4$ are methoxy radicals, $R_1$, $R_3$ and $R_5$ are hydrogen and X is ethylene, Y is methylene; when $R_2$ and $R_4$ are methoxy radicals, $R_1$, $R_3$ and $R_5$ are hydrogen and X is ethenylene, Y is methylene or hydroxymethylene; and when $R_2$ and $R_4$ are benzyloxy radicals, $R_1$, $R_3$ and $R_5$ are hydrogen and X is ethylene or ethenylene, Y is methylene or hydroxymethylene.

30. The compound of claim 29 wherein $R_1$ is hydrogen.

31. The compound of claim 30 wherein $R_2$, $R_3$, $R_4$ and $R_5$, which may be the same or different, are hydrogen, hydroxyl, halogen, nitro, amino, alkyl of from 1 to about 3 carbon atoms, alkenyl of about 3 carbon atoms, or the radical —OR' wherein R' is lower alkyl of from 1 to about 3 carbon atoms, alkenyl of about 3 carbon atoms, phenyl or benzyl.

32. The compound of claim 31 wherein $R_3$ and $R_5$ are hydrogen.

33. The compound of claim 32 wherein $R_2$ and $R_4$, which may be the same or different, are hydrogen, methoxy radical or benzyloxy radical.

34. The compound of claim 33 wherein $R_2$ and $R_4$ are benzyloxy radicals.

35. The compound of claim 34 wherein X is ethylene and Y is hydroxymethylene.

36. The compound of claim 33 wherein $R_2$ and $R_4$ are hydrogen.

37. The compound of claim 36 wherein X is ethylene and Y is hydroxymethylene.

38. The compound of claim 33 wherein $R_2$ and $R_4$ are hydroxyl.

39. The compound of claim 38 wherein X is ethylene and Y is hydroxymethylene.

40. The compound of claim 29 wherein Z is hydroxymethylene.

* * * * *

UNITED STATES PATENT AND TRADEMARK OFFICE
CERTIFICATE OF CORRECTION

PATENT NO. : 5,041,610
DATED : August 20, 1991
INVENTOR(S) : Keith A. Drengler

It is certified that error appears in the above-identified patent and that said Letters Patent is hereby corrected as shown below: On the Title page In the Title, "Resorcyclic" should read --Resorcylic--

Column 1, line 1, "Resorcyclic" should read --Resorcylic--

Column 4, line 22, "of 5 from" should read --of from--

Column 6, line 13, "7, (2,4-dibenzyloxy" should read --2,4-dibenzyloxy--

Column 7, line 66, "(CDC$l_1$)" should read --(CDC$_3$)--

Column 9, line 38, following "2857," insert --1673,--

Signed and Sealed this

Twenty-ninth Day of December, 1992

Attest:

DOUGLAS B. COMER

Attesting Officer     Acting Commissioner of Patents and Trademarks